(12) United States Patent
Gillan (10) Patent No.: US 7,819,839 B2
(45) Date of Patent: Oct. 26, 2010

(54) RECLINING BREAST PUMPING SYSTEM

(76) Inventor: Jonathan C. Gillan, 306 E. 15th St., Tempe, AZ (US) 85281

( * ) Notice: Subject to any disclaimer, the term of this patent is extended or adjusted under 35 U.S.C. 154(b) by 1568 days.

(21) Appl. No.: 11/049,523

(22) Filed: Feb. 1, 2005

(65) Prior Publication Data

US 2006/0116632 A1    Jun. 1, 2006

Related U.S. Application Data

(63) Continuation-in-part of application No. 10/993,590, filed on Nov. 19, 2004, now abandoned.

(51) Int. Cl.
A61M 1/06    (2006.01)
(52) U.S. Cl. .......................... 604/74; 604/75
(58) Field of Classification Search ............ 604/73–76, 604/118–119, 322, 323
See application file for complete search history.

(56) References Cited

U.S. PATENT DOCUMENTS

| | | | |
|---|---|---|---|
| 119,044 A | 9/1871 | Needham | |
| 949,414 A * | 2/1910 | Cunningham | 604/76 |
| 2,364,866 A * | 12/1944 | Meynier, Jr. | 128/890 |
| 3,977,405 A | 8/1976 | Yanase | |
| D251,015 S | 2/1979 | Cone | |
| 4,584,992 A | 4/1986 | Liu | 604/315 |
| D288,004 S * | 1/1987 | Blachly | D24/109 |
| 4,772,262 A * | 9/1988 | Grant et al. | D24/109 |
| 4,857,051 A | 8/1989 | Larsson | 604/74 |
| 5,415,632 A | 5/1995 | Samson | 604/74 |
| 5,514,166 A * | 5/1996 | Silver et al. | 604/74 |
| 5,575,768 A | 11/1996 | Lockridge et al. | 604/74 |
| 5,616,125 A | 4/1997 | Jelks | 604/74 |
| 6,004,186 A | 12/1999 | Penny | 450/36 |
| 6,213,840 B1 | 4/2001 | Han | 450/36 |
| 6,247,996 B1 | 6/2001 | Fields | 450/36 |
| 6,273,868 B1 * | 8/2001 | Nordvik | 604/74 |
| 6,383,164 B1 | 5/2002 | Johansen et al. | 604/74 |
| 6,585,686 B2 * | 7/2003 | Cloud | 604/74 |
| 6,663,587 B2 | 12/2003 | Silver et al. | 604/74 |

(Continued)

FOREIGN PATENT DOCUMENTS

WO    WO 03/013628 A1    2/2003

OTHER PUBLICATIONS

Kontes, "Powder, Offset, Joint," web page printed Sep. 24, 2004 at 15:16.

(Continued)

Primary Examiner—Kevin C Sirmons
Assistant Examiner—Phillip Gray
(74) Attorney, Agent, or Firm—Louis J. Hoffman; Edwin A. Suominen (57) ABSTRACT

A disclosed reclining breast pumping system includes a breast shield that forms a passageway. Material of the breast shield adjacent to a first end of the passageway is shaped to fit over an area surrounding the areola and nipple of a woman's breast. Material of the breast shield that extends from a second end of the passageway is formed into a tube. When the breast shield is fitted onto a woman's breast, the part of the passageway closest to but not touching the nipple of the breast extends in a direction that is non-perpendicular to the areola. Variations and methods are also disclosed.

29 Claims, 7 Drawing Sheets

U.S. PATENT DOCUMENTS

| | | | |
|---|---|---|---|
| 6,673,036 B1 | 1/2004 | Britto | 604/74 |
| 6,689,073 B2 | 2/2004 | Quay | 600/573 |
| 6,764,377 B2 | 7/2004 | Gillan | 450/36 |
| 2001/0044593 A1 | 11/2001 | Lundy | 604/74 |
| 2003/0204164 A1 | 10/2003 | Britto et al. | 604/74 |
| 2005/0112995 A1 | 5/2005 | Gillan | |

OTHER PUBLICATIONS

Grainger, "Funnel Filler, 2 Qt," web page printed Sep. 24, 2004 at 15:17.

Tudor Scientific Glass, "Funnel, Filling, Flat Side, Short Stem, Bottom Joint," web page printed Sep. 24, 2004 at 15:19.

Gerber, "Breastfeeding Products," web page printed from http://www.gerber.com/bf/products/pump/index.html, undated.

Web page printout. "Whittlestone, Breast Expresser,"http://www.whittlestone.com/prod_portablepumb.cfm, undated.

Web page printout. "Ameda, Portable Breast Pumps,"http://www.ameda.com/products/portable.htm, undated.

Web page printout. "Breast-Pump.com; medela; Medela Pump In Style Professional Breastpump," http://www.breast-pump.com, dated as 2001.

Web page printout. "Epinions.com, Review of Hollister PurelyYours Electric Pumb,"http://www.epinions.com/kifm-review, dated as Jan. 15, 2000.

Web page printout. "Mommys Thinkin.com: Whiper Wear Breast Pump,"http://www.momysthinkin.com/whisper_wear_breast_pumps.htm, undated.

"Pump in Style Breastpumps: Instructions for Use," dated as 2002.

Gerber Manual Breast Pump Kit—product packaging, instruction manual, and photographs of product, alone and in use; circa 2002.

Gerber manual flange with bottle fitting (part of product)—photographs of product, alone and in use; circa 1990's.

* cited by examiner

RECLINING BREAST PUMPING SYSTEM

CROSS REFERENCE TO RELATED APPLICATIONS

This application is a continuation-in-part of U.S. application Serial No. 10/993,590 filed Nov. 19, 2004, now abandoned.

BACKGROUND OF THE INVENTION

Conventional breast milk pumping equipment employs breast shields in which milk initially flows in a direction substantially perpendicular to the areola of a nursing woman's breast. For such flow to occur with reasonable efficiency, the breast shield must be oriented without any upward tilt, and preferably with a significant downward tilt, to have gravity assist the flow of expressed milk away from the breast. Given typical positioning of the areola on the nursing woman's breast, however, imparting a downward orientation to a conventional breast shield typically requires the nursing woman to lean forward, or at best, sit upright.

Few women find it comfortable to lean forward for long periods of time while pumping. Indeed, for some nursing women (e.g., recovering surgery patients), leaning forward to make a conventional breast shield work properly can be intensely uncomfortable and even harmful.

Thus, there is a long-felt need for breast-pumping equipment that can be more comfortably used. A reclining posture not only is more comfortable but also, with suitable "hands-free" equipment, can allow the mother to simply relax or engage in relaxing activities such as reading or hand work (e.g., knitting).

Although it does not mention anything about a reclining position, PCT Application No. WO 03/013628 discloses a breast pump "having a funnel with a convergent bell-portion for placing on the breast over the nipple, wherein a tubular outlet of the funnel leading from the bell-portion is angled out of axial alignment with said bell-portion," see page 1, lines 8-12. As there disclosed, the funnel "can be adjusted to take up a variety of orientations to suit the woman concerned in finding a comfortable position for holding and operating the pump," page 1, lines 21-24. The "axial misalignment" is disclosed to be within a range of 20 to 40 degrees, with specific mention of 30 degrees, see page 1, lines 20-28. However, this disclosure remains unsatisfactory because the portion of the passageway closest to the breast has an orientation perpendicular to the areola, which would still point upward if the woman were in a reclining position.

U.S. Pat. No. 6,585,686 specifically mentions the desire to use a breast pump while in a reclining position (see column 1, lines 29-54) and attempts to address that need by providing a "bypass path" including a "bypass tube, pipe or other conveyance." As disclosed, the bypass path collects milk from a part of a breast shield that is well below a nursing woman's nipple during use. The bypass path provides for delivery of milk in addition to, or instead of, a main delivery tube when the nursing woman is sitting in a reclining position, see column 4, lines 37-64. However, it remains desirable to collect breast milk in the reclining position directly from the nursing woman's nipple, without relying on transit of milk across her breast to some other position.

It would also be desirable to avoid a concentration of pressure at the base of the nursing woman's nipple, stretching of the nipple into the tube, and the pain and milk duct stress that both of those undesirable actions often induce in conventional breast shields. The tube that a conventional breast shield includes for conveying milk from the nipple is typically sized to be just large enough for the nipple to be pulled into it, responsive to pumping suction. A sharply defined, ring-like boundary typically exists between the tubular outlet and the flared remaining portion of the breast shield. In use, the areola and the less sensitive fatty tissue surrounding it are held in a constant state outside of that ring while the nipple alone is pulled into the tube. With each onset of pumping suction, more and more of the nipple is often pulled in, resulting in increased pain at the ring area for the nursing woman.

Further, it would be desirable to have a convenient, compact, and lightweight support system for "hands-free" breast milk expression, in which firm contact with one or both breasts could be established without the need for the nursing woman to maintain that contact by hand.

SUMMARY OF THE INVENTION

A reclining breast pumping system according to various aspects of the present invention includes a breast shield that forms a passageway. Material of the breast shield adjacent to a first end of the passageway is shaped to fit over an area surrounding the areola and nipple of a woman's breast. Material of the breast shield that extends from a second end of the passageway is formed into a tube. When the breast shield is fitted onto a woman's breast, the part of the passageway nearest the nipple but not touching the breast during use extends in a direction that is non-perpendicular to the areola of the breast.

According to a particularly advantageous aspect of the invention, the part of the passageway nearest the nipple but not touching the breast during use is elliptical in a cross-section that lies parallel to the plane of the areola of the breast. A part of the passageway referred to herein as an "interface" is the part of the breast shield where the milk flows out of the nipple and begins entering the tube leading to the second end of the passageway. There, the breast shield gradually narrows from the wider part of the shield surrounding the nipple and areola to the narrower portion that is the tube.

When the interface is elliptical and formed into a particularly desirable shape, with a length that is about twice its width, nipple and areola soreness seem to be significantly reduced as compared to what is typically encountered with a conventional circular interface. Constriction of milk ducts also seems to be alleviated with such an interface. Applicant suspects that the improvement is due, at least in part, to a similarity between the elliptical interface's shape and the natural shape of a nursing infant's mouth. That shape avoids presenting an abrupt, ring-shaped boundary around the nursing woman's nipple. The normal suckling of an infant is such that the infant's lips are well past the nipple and create a suction seal at the less sensitive breast region there. The nipple and areola, subjected mostly to stimulation by the tongue, float relatively freely in the infant's mouth with little if any discomfort to the nursing woman. Allowing some free movement of the areola and nipple relative to the material of the breast shield advantageously facilitates natural drainage of milk ducts in the breast.

The fit between the interface and nipple size also becomes less critical with an elliptical shape than with a circular one, and residual soreness can be alleviated by slight rotation of the breast shield to change points of contact between edges of the interface and the areola. In addition, an elliptical interface (as compared to a conventional circular interface) and gradual passageway transition at the interface reduce concentration of suction force on the woman's areola and likely helps avoid irritation to, and compression of, milk ducts. Indeed, suction is applied some distance away from the nipple and immediately surrounding areola, and the uncomfortable and potentially counterproductive stretching of the nipple is avoided. With reduced discomfort, the woman using the breast shield is better able to relax, which likely aids the lactation response.

The part of the passageway that is nearest to but not touching the nipple during use extends in a direction that can be between about 20 and 40 degrees from perpendicular to the areola. Preferably, the direction is between about 25 and 30 degrees from parallel from perpendicular to the areola, most preferably about 26 degrees from perpendicular to the areola.

According to another aspect of the invention, the material of the breast shield that is adjacent to the first end of the passageway, i.e., the material nearest the widest part of the breast shield, includes a number of ripples at varying radii about the first end of the passageway. Advantageously, such ripples help the breast shield material maintain firm contact with the breast skin during the pumping cycle while providing a massaging action during high-suction parts of the cycle.

A method of the invention employs a breast shield that includes a passageway, as discussed above, or a pair of such breast shields. In no particular order, each breast shield is fitted onto a woman's breast and the woman assumes a reclining position, i.e., leaning back comfortably without being entirely prone. The part of each breast shield's passageway nearest to the nipple of the breast on which it is fitted extends in a direction that is non-perpendicular to the areola of the breast and, consequently, remains downward despite the reclining position. By keeping the part of the passageway nearest to the nipple aimed in a downward direction, the method facilitates the gravity-induced flow of milk and avoids pooling.

The above summary does not include an exhaustive list of all aspects of the present invention. Indeed, the inventor contemplates that the invention includes all systems and methods that can be practiced from all suitable combinations of the various aspects summarized above, as well as those disclosed in the detailed description below and particularly pointed out in the claims filed with the application. Such combinations have particular advantages not specifically recited in the above summary.

DESCRIPTION OF PREFERRED EXEMPLARY EMBODIMENTS

A reclining breast pumping system according to various aspects of the present invention is illustrated in the figures. As may be better understood with reference to FIG. 1, for example, one such system 100 includes: a strap 110 comprised of strap material that suspends from the neck 152 of a nursing woman, wearer 150; a pair of angled breast shields 122, 124; and a pair of flexible cords 132, 134 that support breast shields 122, 124 at breasts 162, 164, respectively, of wearer 150. Cords 132, 134 connect opposite ends of strap 110 to trapeze support structures 142, 144 to support breast shield 122, 124, respectively.

Figure 1:
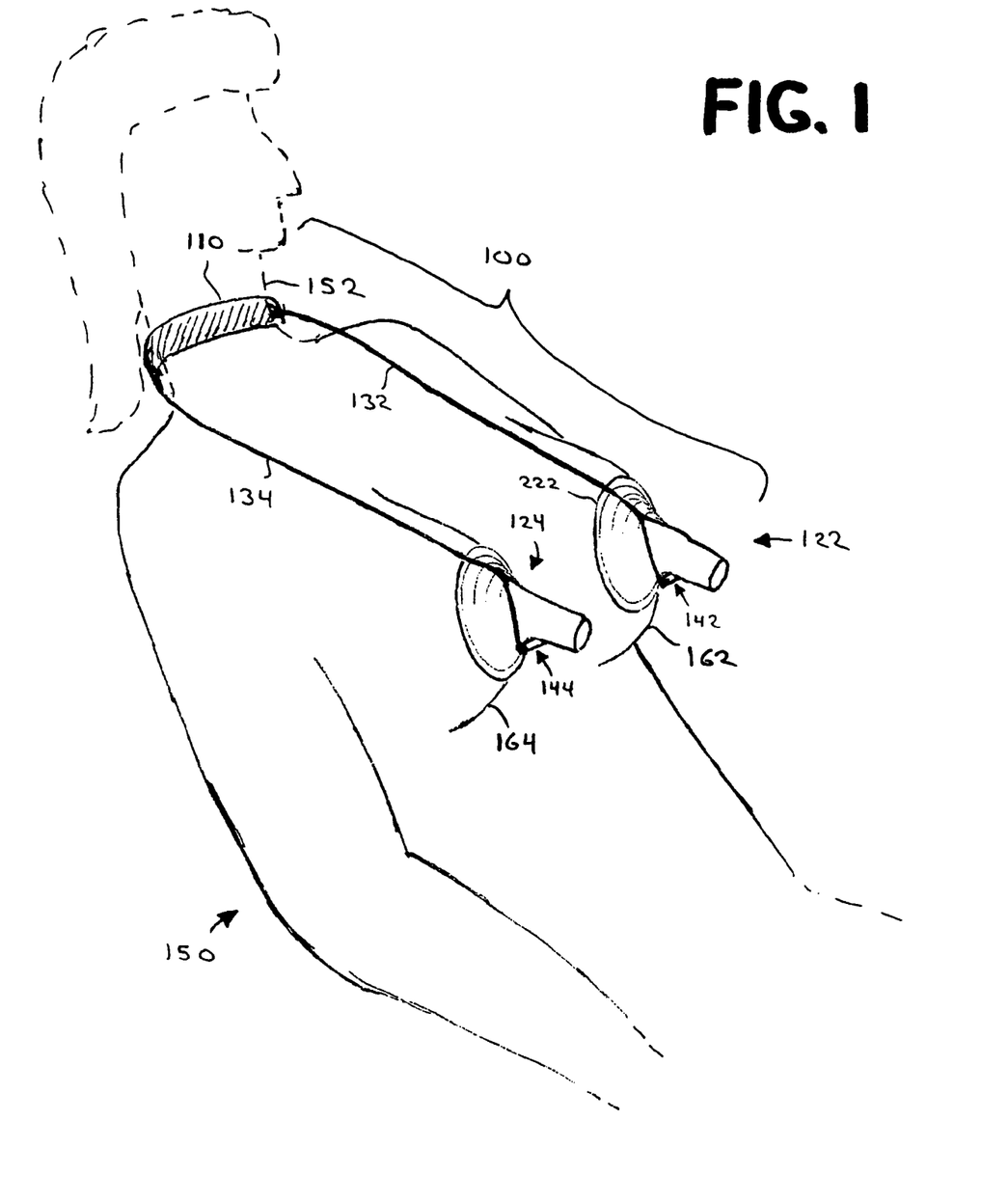
FIG. 1 is a perspective view of a pair of angled breast shields with trapeze supports and a neck strap in a hands-free arrangement according to various aspects of the invention.

FIG. 1 illustrates wearer 150 in a partially reclining position. There is a structural benefit to the reclining position, in addition to its increased comfort for wearer 150, because it permits the weight of breast shields 142, 144, and whatever conventional apparatus (not shown) is employed for milk collection and suction, to help keep breast shields 142, 144 firmly in contact with breasts 162, 164.

A breast shield according to various aspects of the invention includes any structure suitable for contacting a nursing woman's breast and passing expressed milk from the breast through the breast shield to some type of collection device (not shown), e.g., a milk bottle with a Venturi suction device near its neck. Angled breast shields 122, 124 are particularly advantageous in that they have portions for breast contact and milk passage that are angled with respect to each other.

Figure 2:
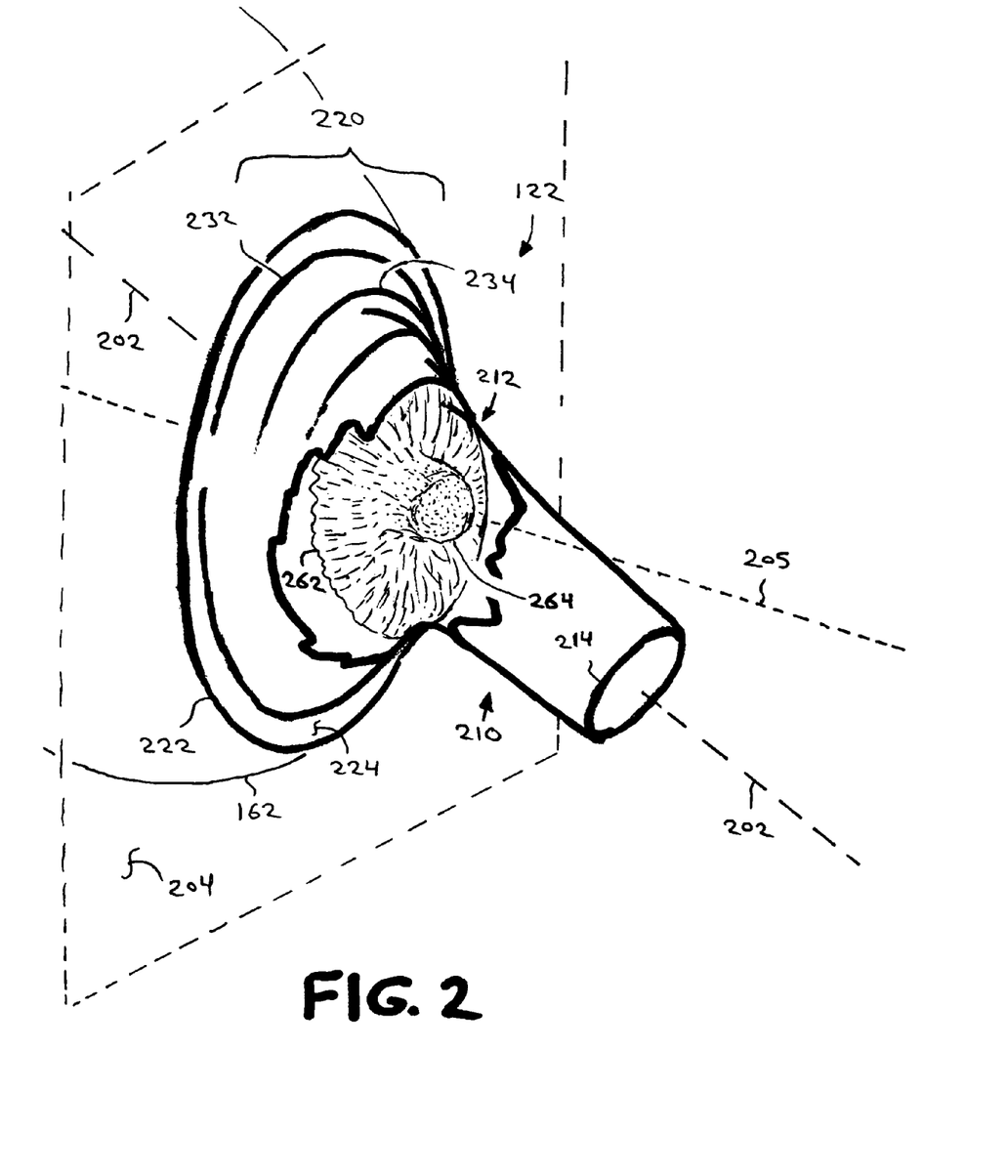
FIG. 2 is a perspective cutaway view of one of the angled breast shields of FIG. 1 fitted onto a breast.
Figure 3:
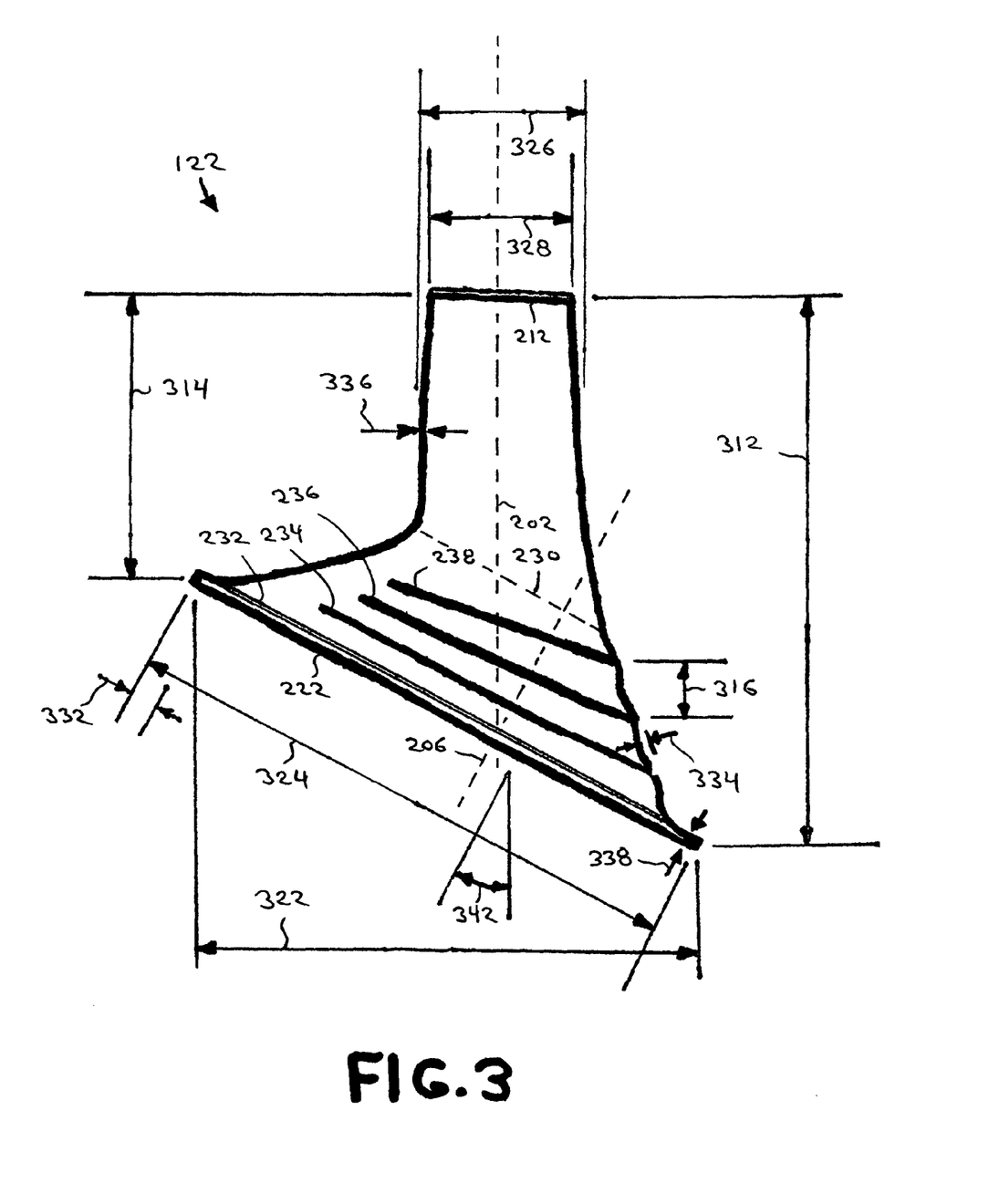
FIG. 3 is a cutaway side view of the angled breast shield of FIG. 2.
Figure 4:
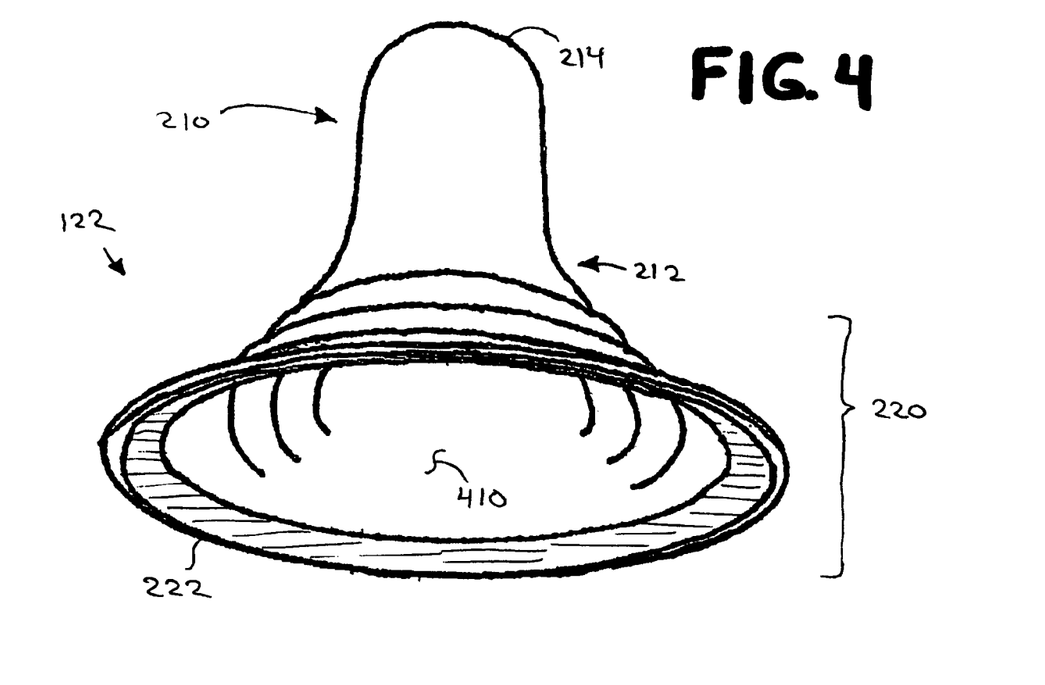
FIG. 4 is a perspective view of the angled breast shield of FIG. 2 as seen from above and behind the breast shield.
Figure 5:
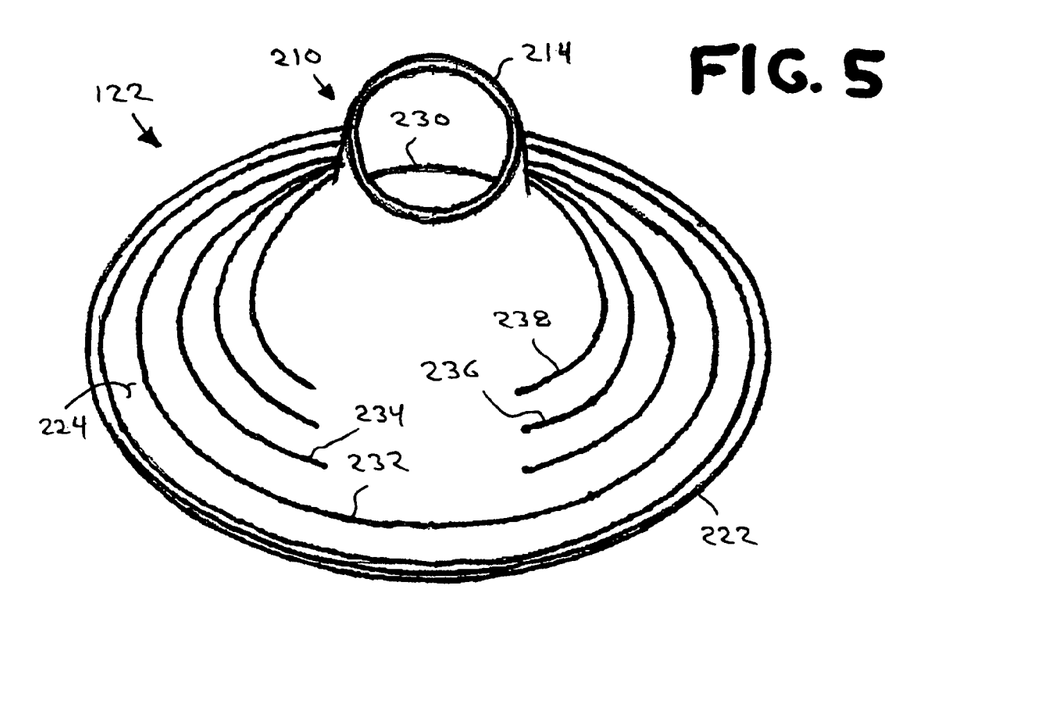
FIG. 5 is a perspective view of the angled breast shield of FIG. 2 as seen from below and in front of the breast shield.

As may be better understood with reference to FIGS. 2-3, breast shield 122 (which can be substantially identical to breast shield 124) forms a passageway, with material adjacent to one end 222 of the passageway forming a flange 220 and material extending from the other end 214 of the passageway forming a tube 210. The material of breast shield 122 that forms flange 220 is shaped to fit onto a woman's breast around the nipple. As FIG. 2 illustrates, breast shield 122 fits onto breast 162 around its nipple 264.

Figure 7:
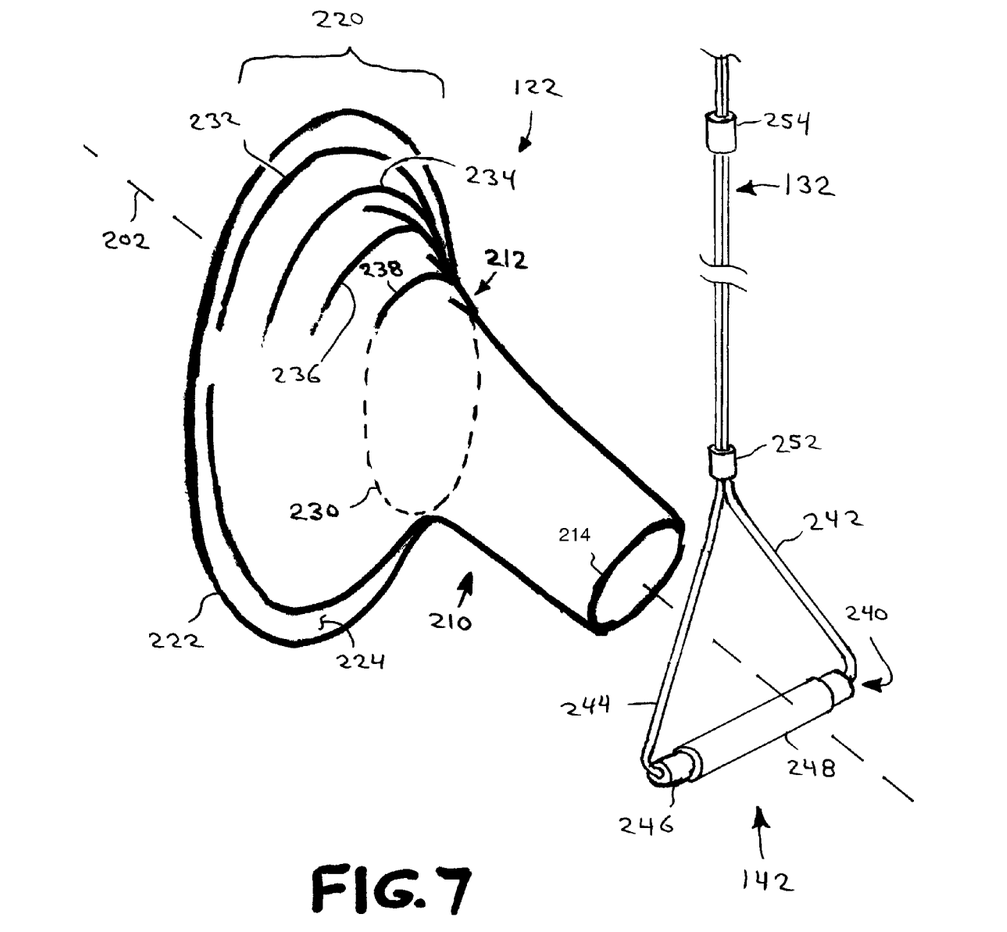
FIG. 7 is a perspective view of one of the trapeze supports of FIG. 1 with a perspective view of the angled breast shield of FIG. 2 illustrating an elliptical interface between the shield's major flange and tube structures.

As may be better understood with reference to FIG. 7, tube 210 and flange 220 of breast shield 122 merge at an interface 230, where the flow of milk transitions to the portion of the passageway of breast shield 122 that begins roughly around region 212 and terminates at end 214. Part 212 of the passageway is the part generally nearest nipple 264 (but not touching nipple 264 or breast 162) during use, as illustrated in FIG. 2. In cross-section, in a plane 204 parallel to areola 262, interface 230 has a roughly elliptical shape. A gradual change in surface orientation of the material of breast shield 122 from tube 210 to flange 220 helps ensure that interface 230 presents no abrupt edges that would put uncomfortable, concentrated pressure on breast 162 during use.

Plane 204 is substantially angled from a plane perpendicular to the axis 202 of tube 210. Axis 205 defines a line along which nipple 264 points. For typical breasts, axis 205 is perpendicular to plane 204. Typically, when breast shield 122 is placed over an area surrounding areola 262 and nipple 264 of breast 162, flange end 222 may lie in a plane (not shown) that is generally parallel to plane 204 of areola 262. Some passageway ends (either a flange end or a tube end) will not lie in a single plane. For example, flange end 222 can depart from coplanarity with plane 204 because of tabs, flaps, or other structures unrelated to milk expression functions.

Flange 220 terminates in a chest ring 224, which angles away from the otherwise generally conical surface of flange 220 to avoid having sharp edges contacting the breast.

The material of a breast shield of the invention can have two or more (preferably, three or more) ripples in its surface or wall. Such ripples provide an area where suction can form, advantageously helping the breast shield maintain firm contact with the breast skin during low-suction parts of a pumping cycle while providing a massaging action during high-suction parts of the cycle. The ripple can be formed from any suitable type of indentation, protuberance, or combination of the two.

In exemplary breast shield 122, as seen in FIG. 3, the surface of flange 220 includes four ripples 232, 234, 236, 238. The outermost ripple 232 is at an edge of flange 220, where it joins chest ring 224. The innermost ripple 238 is at another edge of flange 220, where it joins tube 210 at interface 230. Ripples 234, 236 lie between ripple 238 and ripple 232.

FIGS. 1-5, 7 illustrate ripples 232, 234, 236, 238 by lines tracing the outermost protrusions of the ripples. Preferably, the lines (which FIGS. 1-5, 7 show only for clarity of illustration) do not actually appear as distinct surface indicia on flange 220.

When suction in breast shield 122 is low, skin of breast 162 (FIG. 2) is permitted to pull away from the wall of flange 220 between ripples 236, 238. The protrusion of ripple 236 can be expected to remain substantially in contact with the skin and preserve suction in the part of flange 220 between ripple 236 and end 222. The protrusion of ripple 234 is even more likely to remain in contact with the skin and preserve suction in the region between ripple 234 and end 222.

When suction in breast shield 122 increases during the pumping cycle, most skin near areola 262 is pulled inward toward tube 210. The ripples resist the pulling force, distributing it over a larger surface area than just the skin that comes in contact with flange-tube interface 230 (FIG. 7). In addition, the texture of ripples 232, 234, 236, 238 in combination with the cyclic pulling motion of the pumping cycle provides a soft massage to the breast, possibly contributing to overall milk production.

According to various aspects of the invention, the indentations or protrusions of the ripples form substantially concentric rings. Exemplary ripples 232, 234, 236, 238 of breast shield 122 (FIGS. 2-5) have their indentation or protrusion (or both, for ripples having such) extending along only a portion of some circle having the ripple's center and radius. The ripples can extend part way or completely around breast shield 122.

Advantageously, breast shield 122 has no ripples in an area 410 (FIG. 4) that lies adjacent to areola 262 during normal use. There, the mass of breast 162 helps keep the skin in firm contact with the wall of flange 220 even without regard to suction. The reduced attachment force helps wearer 150 to remove breast shield 122 from breast 162 when some suction remains inside breast shield 122.

The tube of a breast shield according to various aspects of the invention includes any conduit structure suitable for conveying milk from the nipple of a nursing woman's breast. The tube may end close to the breast, as in the depicted embodiments, or continue for some distance away from the breast. In particular, shield 122 may be formed with its tube end 212 mating with another milk line or tube (not shown) further extending to the milk bottle in which milk is collected. Alternatively, such an additional line may be formed integrally with shield 122. The use of the term "end," consequently, can mean a place where the material ends, wherever located, without regard to whether further material is fitted, at some times, in contact with the end. In the integrally formed embodiment, the "end" could simply be the place where the line fits into the cap of the bottle (not shown). The "end" can even be the cap of the bottle itself, if the cap is formed integrally with the line.

In exemplary breast shield 122, material of tube 210 lies substantially in a cylindrical wall that is a surface of revolution about axis 202. Axes 202 and 205 are geometrical abstractions of physical features (e.g., lengthwise orientation) of tube 210 rather than physical features themselves. Exemplary variations (not shown) of tube 210 may slightly arc (e.g., having a banana shape), undulate, or taper rather than having exactly cylindrical walls. In that case, axis 202 should be defined as the line that would best fit as an axis, such that the deviation of walls 210 from axis 202 is minimized. Tube 210 may be flexible, in which case axis 202 should be defined as the line that would fit the beginning of the passageway (the portion closest to the nipple in use, at part 212) when the tube is straightened or in its most relaxed, least kinked, state.

When breast shield 122 is fitted onto a breast of woman 150, the part 212 of the passageway of breast shield 122 nearest nipple 264 extends in a direction non-perpendicular to areola 262 (or plane 204). Thus, axes 202 and 205 are oriented to form an angle between them. The figures illustrate exemplary breast shield 122 with the entire length of tube 210 extended in that direction. However, only the part nearest part 212, long enough to prevent significant pooling of milk inside breast shield 122, need do so. The angle between the axes 202 and 205 is referred to herein as the tube deviation angle.

Angling tube 210 provides significant benefits, particularly at preferred tube deviation angles. In exemplary system 100 (FIGS. 1-2), tube 210 of breast shield 122 extends downward with respect to flange 220 and provides a downward passage for expressed breast milk, allowing gravity to work even when wearer 150 partially reclines.

Both the desired reclining angle and the angle at which flange 220 fits the breast can vary significantly for different nursing women. A tube deviation angle in a range between about 20 degrees and about 40 degrees is expected to provide some benefit for most nursing women. For nursing women having certain vertically elevated areolas, however, a tube deviation angle at the lower end of that range would preclude any significant downward orientation of the tube in typical reclining poses.

Advantageously, a variety of breast shields can offer different tube deviation angles. Higher deviation angles are of more benefit for nursing women who favor deeply reclining poses or who have certain vertically elevated areolas. Lower deviation angles are of more benefit to nursing women who prefer more upright posture or who have areolas with considerable downward orientation. A breast shield having its tube deviation angle in a range between about 25 degrees and about 30 degrees is expected to provide benefit for most nursing women, while tube deviation angles of less than about 10 degrees provide no significant benefit. Particularly advantageous is a tube deviation angle of about 26 degrees.

As FIG. 7 illustrates, any substantial tube deviation angle results in an interface 230 between tube 210 and flange 220 that is a noticeably elliptical in a plane perpendicular to axis 205, even if tube 210 has a substantially circular cross-section.

A breast shield, or pair of breast shields, can be supported at the breasts of a nursing woman by any suitable structure, including the nursing woman's hands. However, the use of a "hands free" support structure provides significant benefits in reducing fatigue and freeing the nursing woman's hands for other activities such as holding a book. In system 100 of FIG. 1, for example, strap 110, flexible cords 132, 134, and trapeze support structures 142, 144 cooperate to provide a comfortable, lightweight support for breast shield 122, 124 that compacts to very small size when not in use and is convenient for the wearer to put on and take off.

Figure 6:
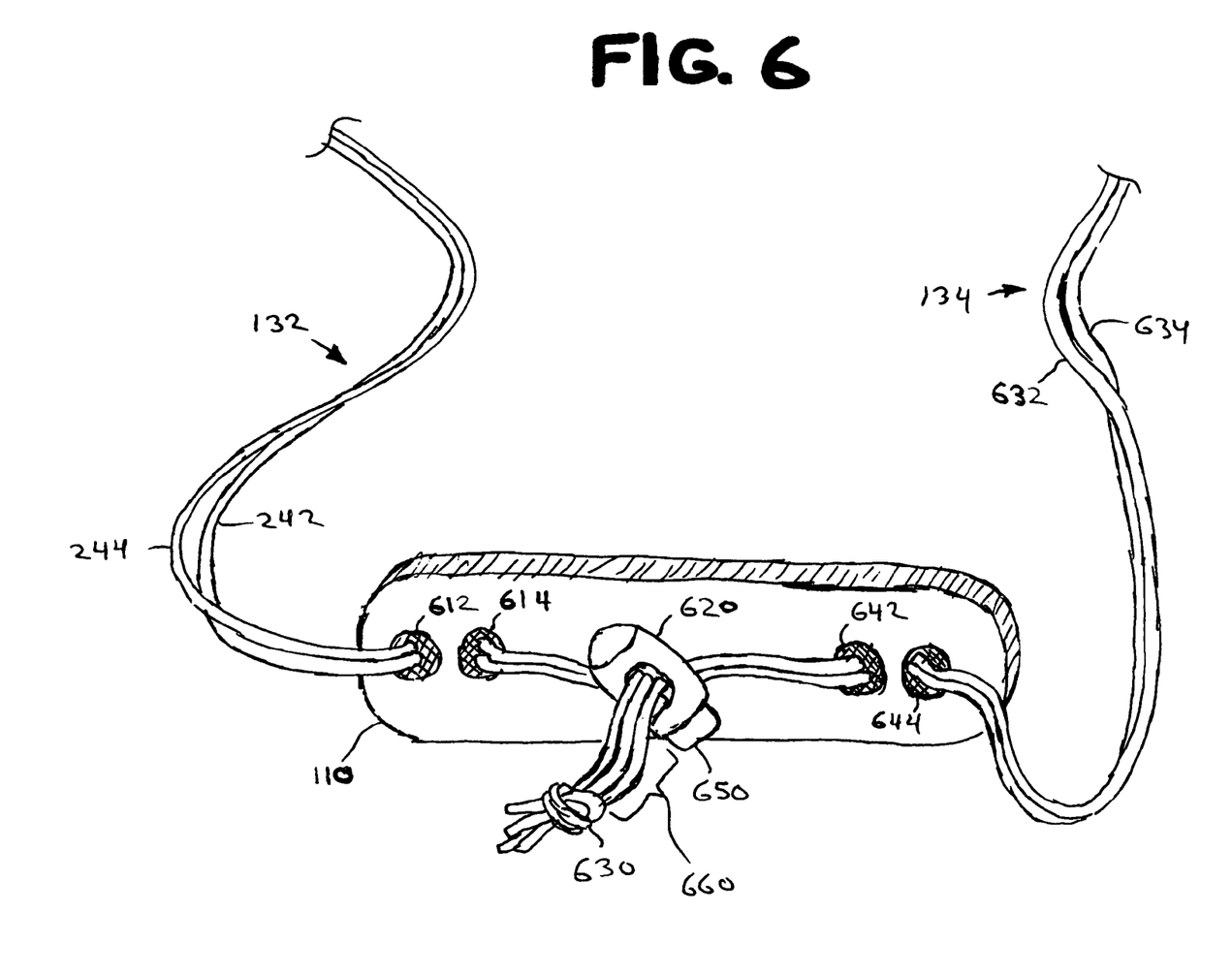
FIG. 6 is a perspective view of the neck strap of FIG. 1 with connecting cords.

As may be better understood with reference to FIG. 6, exemplary neck strap 110 includes a pair of holes 612, 614 at one end and another pair of holes 642, 644 at an opposite end. Strap 110 can be fabricated from neoprene foam of about ⅛-3/16 inch thickness. Flexible cord 132 is made up of a pair of cords 242, 244 that pass through holes 612, 614 and meet up with similar cords 632, 634 of flexible cord 134 in a knot 630. Cords 242, 244, 632, 634, which can be of braided nylon material having about ⅛ inch thickness, all pass through a releasable friction device 620. For fitted support of breast shields 142, 144, wearer 150 can adjust the length of flexible cord 132, 134 between neck strap 110 and trapeze supports 142, 144 (FIG. 1) by adjusting the length of cords 242, 244, 632, 634 that lie in a section 660 beyond friction device 620.

Flexible cords according to various aspects of the invention can be made up of more or fewer cords than the pairs 242, 244 and 634, 634 that make up flexible cords 132, 134. Such cords can connect together in a termination that is provided by a clamp or a weld of melted fibers instead of knot 630, or not connect in any common termination at all.

A releasable friction device according to various aspects of the invention includes any structure for frictionally connecting flexible cords together such that the cords can be released or the point of contact adjusted as desired. Exemplary friction device 620 includes a spring-loaded plunger 650 that wearer 150 can depress with her thumb to release pressure on cords 242, 244, 632, 634. Suitable variations of a releasable friction device include a rubber band, a clip, and a section of semi-rigid wire (e.g., a bread-bag tie) for wrapping around the cords.

A flexible cord can connect a breast shield to a flexible strap by any suitable structure. As may be better understood with reference to FIG. 2, for example, flexible cord 132 terminates in a trapeze support structure 142 that fits around tube 210 of breast shield 122 to support it. (As FIG. 1 illustrates, flexible cord 134 has the same type of termination.)

Trapeze support structure 142 has a triangular shape, with one side being made up of a bar 240 and the other sides being cords 242, 244 of flexible cord 132, split at retaining sleeve 252, which can be slid down cord 132 to secure it around tube 210. Other optional retaining sleeves (one of which, sleeve 254, is shown) can be spaced along flexible cord 132 further away from trapeze support structure 142, e.g., at regular intervals. Alternatively, other sleeves can be omitted.

Exemplary bar 240 is made up of an inner sleeve 246 fabricated from machined aluminum or stainless steel and an outer sleeve 248 fabricated from a medical grade neoprene rubber. Friction between rubber outer sleeve 248 and tube 210 helps keep breast shield 122 from moving side to side with respect to trapeze support structure 148.

Cord 242 passes into inner sleeve 246 and emerges as cord 244. In exemplary system 100, cords 242, 244 are actually segments of a single, continuous length of cord, although such is not required.

Figure 8:
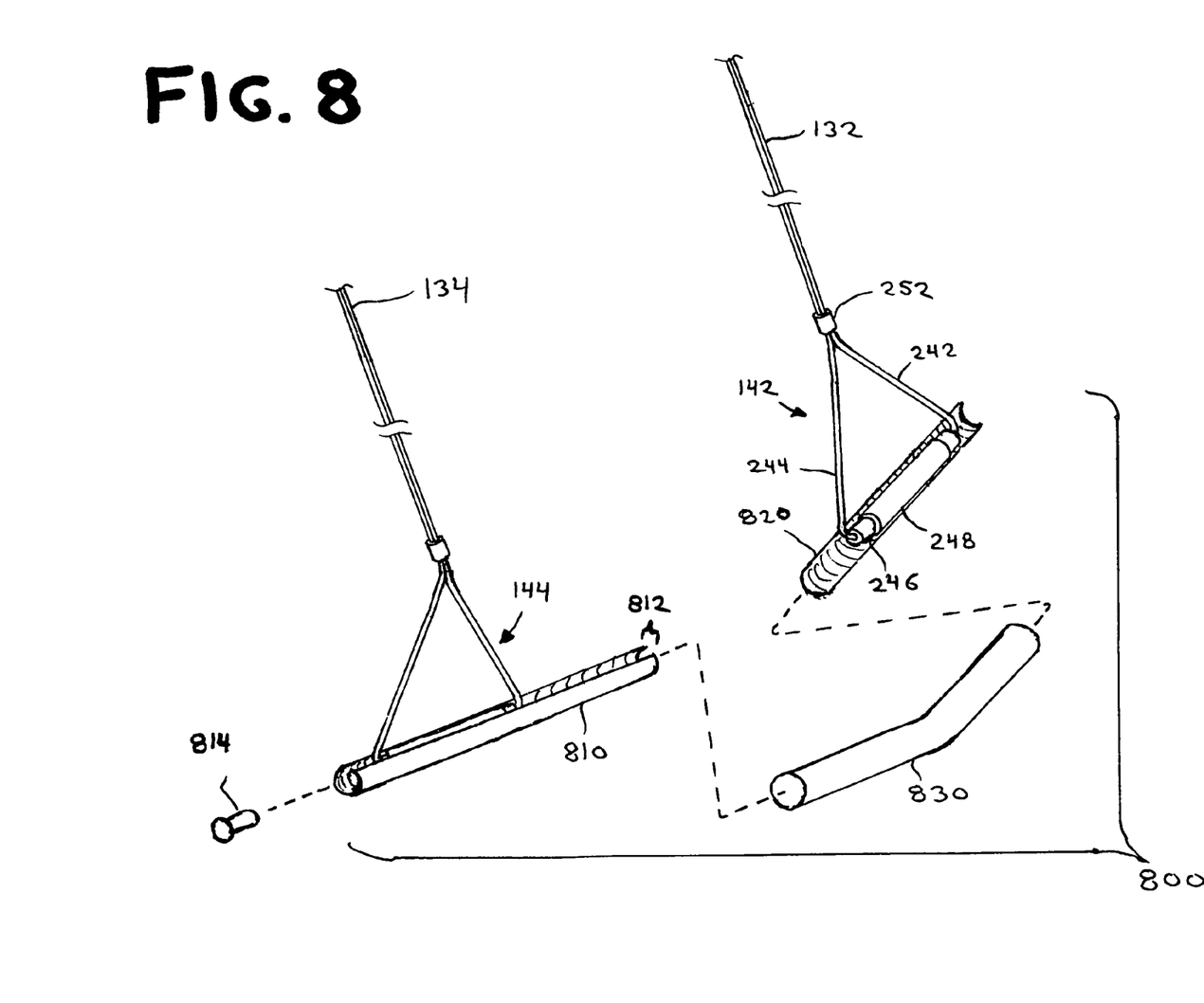
FIG. 8 is a perspective view of a pair of trapeze supports and components of a connecting bar structure according to various aspects of the invention.

Advantageously, a pair of breast shields can connect together via a substantially rigid bar, as disclosed in U.S. Pat. No. 6,764,377 to Gillan, which is incorporated herein by reference. FIG. 8 illustrates an exemplary structure 800 that can be employed to connect trapeze support structures 142, 144 of reclining breast pumping system 100 together. When they support breast shields 122, 124 (FIG. 1) in that configuration, structures 142, 144 connect breast shields 122, 124 of system 100 together.

Structure 800 includes a pair of straight bar sections 810, 820 that are joined together by a bent bar section 830. The partially cutaway view of FIG. 8 illustrates how outer sleeve 248 of trapeze support structure 142 fits snugly inside bar section 820. Cords 242, 244 pass into bar section 820 through a slot that runs lengthwise along it and meet inside outer sleeve 248. FIG. 8 does not show that slot because it omits illustration of a substantial portion of bar section 820, but it does illustrate a similar slot 812 in bar section 810. Preferably, the slots are just wide enough to accommodate cords 242, 244 of support structure 142 and counterpart cords of trapeze support structure 144.

Bar sections 810-830 can be fabricated from any suitably thin, hollow structure, e.g., thin-walled, transparent polystyrene. Polystyrene tubing having a wall thickness of 0.05 inch and an inside diameter of 0.215 inch can be employed. Sections 810, 820 should fit snugly inside opposite ends of bar section 830. When the desired distance between support structures 142, 144 is smaller, e.g., to fit a nursing woman having a narrower frame, bar section 830 can be omitted. In that case, one of bar sections 810, 820 can fit inside an end of the other, or a shorter bar section (not shown) can be employed to provide a mutual point of connection. In either case, plastic plugs like plug 814 of a desired color (e.g., white) can be inserted into the ends of bar sections 810, 820 to improve overall appearance of structure 800 and keep trapeze support structures 142, 144 inside it.

Various particular features of exemplary breast pumping system 100 may be better understood with reference to the labeled paragraphs below. In variations where the benefits of these particular features are not required, they may be suitably omitted or modified while retaining the benefits of the various aspects of the invention discussed above. Structural elements not introduced with a reference numeral are generally not illustrated in the drawings. Those structural features referenced by number are illustrated in FIG. 2 unless otherwise indicated.

DIMENSIONS—Listed in TABLE I below are presently preferred "one size fits all" dimensions of breast shield 122. The table's left column contains reference numerals that label structure of FIG. 3 as having the dimensions provided in respective entries of the right column. The table's middle column provides a brief description of each dimension.

TABLE I

| Dimension | Description | Measurement |
| --- | --- | --- |
| 312 | Overall length | 3.5 inch |
| 314 | Tube length | 1.9 inch |
| 316 | Ripple spacing (along axis 202) | 0.4 inch |
| 322 | Overall width | 3.0 inch |
| 324 | Flange end width | 3.5 inch |
| 326 | Tube origin width | 1.0 inch |
| 328 | Tube end width | 0.9 inch |
| 332 | Chest ring width | 0.2 inch |
| 334 | Ripple depth | 0.1 inch |
| 336 | Wall thickness | 0.05 inch |
| 338 | Chest ring wall thickness | 0.125 inch |
| 342 | Tube deviation angle | 26° |

CENTERLINE OFFSET—As FIGS. 2-3, 7 illustrate, tube 210 is positioned such that its axis 202 passes through flange end 222 somewhat displaced from center. The centerline offset of tube 210 resulting in that displacement helps reduce the amount of volume contained inside breast shield 122 at interface 230 on what is likely to be the downward side of breast shield 122 during use. This reduced volume helps prevent pooling of milk within breast shield 122.

AESTHETICS—Trapeze support structure 142 has a distinctive appearance when its components have a highly contrasting white and black color scheme. In such a color scheme, inner sleeve 246 is white and retaining sleeves 252, 254 (and others not shown) are white or silvered. Outer sleeve 248 is black, as are cords 242, 244.

ADDITIONAL SURFACE FEATURES—A breast shield according to various aspects of the invention can include particular features such as surface indicia or texturing. For example, breast shield 122 can include a group of five to ten closely spaced, shallow indentations on the portion 410 (FIG. 4) of its inner surface of its flange 220 where ripples 232, 234, 236, 238 do not extend. The indentations can form a pattern that is purely decorative, or they can be pronounced enough to hold the bottom of breast 162 stationary within breast shield 122.

BREAST SHIELD FABRICATION—Breast shield 122 can be manufactured by injection molding from a medical-grade polypropylene. The mold can be made up of two high-strength steel halves that have had voids machined (including a central "pole" for the shield's interior space) to match the reverse of the breast shield with its ripples, flange and tube, chest ring, etc. Care and craftsmanship should go into the making of the mold so that each half fits with the other in good alignment. The mold should incorporate effective ejector pins, which can push each molded breast shield from the cavity once the mold is opened and the fabricated breast shield has cooled sufficiently.

ALTERNATIVE MODES OF USE—nursing women can advantageously use a breast shield according to various aspects of the invention in different positions than that illustrated in FIG. 1. For example, a nursing woman whose areolas point generally downward may benefit from the tube-flange deviation of breast shield 122 by using it in essentially a reversed orientation. In that mode of use (not shown), breast shield 122 has its end 222 facing upwards toward the areola and its angled tube 210 extending downward and in a desired azimuthal direction, e.g., off to the nursing woman's side.

As another example, a nursing woman who is recovering from surgery or is otherwise bedridden can express milk from one breast at a time while lying down. In that mode of use (not shown), breast shield 122 can have its flange end 222 lying in a substantially vertical plane and its angled tube 210 oriented downward and somewhat away from the nursing woman.

USE WITH BREAST PUMPING PRODUCTS—Breast shield 122 can be inserted into a conventional breast pump flange, e.g., the AMEDA pump marketed by Hollister, Inc. of Liberty, Ill., or the standard flange and pump marketed by Medela, Inc. of McHenry, Ill. It can also entirely replace the flange of a suitable type of breast pump, e.g., the PERSONAL FIT product marketed by Medela, Inc.

Public Notice Regarding the Scope of the Invention and Claims

No one embodiment disclosed herein is essential to the practice of another unless indicated as such. Indeed, the invention, as supported by the disclosure above, includes all systems and methods that can be practiced from all suitable combinations of the various aspects disclosed, and all suitable combinations of the exemplary elements listed. Such combinations have particular advantages, including advantages not specifically recited herein.

Alterations and permutations of the preferred embodiments and methods will become apparent to those skilled in the art upon a reading of the specification and a study of the drawings. For example, although the breast shields disclosed above includes a flange and tube that are comprised of different portions of the same piece of material, a breast shield can have a flange and tube made of different materials, or separate fabrications of the same material, connected together at an interface, e.g., with glue or melt-bonding. Such a configuration may be advantageous where different material characteristics are desired for the flange than for the tube, e.g., in a breast shield having a flange made of pliable silicone rubber and a rigid, structurally supportive tube.

Accordingly, none of the disclosure of the preferred embodiments and methods defines or constrains the invention. Rather, the issued claims variously define the invention. Each variation of the invention is limited only by the recited limitations of its respective claim, and equivalents thereof, without limitation by other terms not present in the claim. For example, a claim generically reciting ripples reads on claims to devices including ripples with only indentations, ripples with only protuberances, and ripples with both types of surface or wall feature.

In addition, aspects of the invention are particularly pointed out in the claims using terminology that the inventor regards as having its broadest reasonable interpretation; the more specific interpretations of 35 U.S.C. § 112(6) are only intended in those instances where the terms "means" or "steps" are actually recited. For example, claims reciting material of a breast shield that is formed into "a tube" are not intended to be limited to a perfectly cylindrical, rigid, straight tube having a constant inside or outside diameter. As another example, claim limitations reciting a part of the tube "nearest" to one end or object are intended to specify a part of the tube's material that is closer to that end or object than any other region. Recitation of a "part" of some size, rather than just some speck of material, may be required in some claims to provide a meaningful frame of reference, e.g., for limitations involving a direction in which a tube extends. Recitation of nipple or areola movement relative to material of a breast shield refers to position shifting of those anatomical parts that can occur even when the breast shield is firmly in place on the breast, due to pliability of the breast.

The words "comprising," "including," and "having" are intended as open-ended terminology, with the same meaning as if the phrase "at least" were appended after each instance thereof. A clause using the term "whereby" merely states the result of the limitations in any claim in which it may appear and does not set forth an additional limitation therein. Both in the claims and in the description above, the conjunction "or" between alternative elements means "and/or," and thus does not imply that the elements are mutually exclusive unless context or a specific statement indicates otherwise.

What is claimed is:

1. A method for a woman to express breast milk, comprising:
   (a) placing a breast shield over an area centered on the areola and nipple of a breast of the woman, wherein:
      (1) the breast shield comprises
         (i) a flange shaped to fit over the area centered on the areola and nipple while allowing nipple and areola movement relative to the flange; and
         (ii) a tube extending from the flange at a portion of the flange encircling the nipple;
      (2) the flange and tube form a common passageway;
      (3) the passageway surrounding the nipple when the shield is fitted onto the breast and suction is applied, extends in a direction substantially non-perpendicular to the areola; and (4) the flange is shaped so that an area of the breast, at least in an area below the nipple, contacts an inner wall of the flange when the breast shield is fitted onto the breast without suction being applied;
(b) orienting the breast shield such that the passageway, at the point surrounding the nipple, extends downward; and
(c) while the passageway is so oriented, expressing milk from the breast through the passageway and the tube while the woman is reclining.

2. The method of claim 1 wherein placing the breast shield further comprises supporting the breast shield by placing the tube through a trapeze support structure, which trapeze support structure is supported from a strap around the woman's neck by a flexible cord.

3. The method of claim 1 further comprising repeating parts (a) through (c) for a second breast shield placed over an area centered on the areola and nipple of the other breast of the woman.

4. The method of claim 3 wherein placing the two breast shields further comprises using a pair of breast shields coupled to the strap with a trapeze support structure and a flexible cord.

5. The method of claim 1 wherein placing the breast shield further comprises using a breast shield structured to allow the passageway to contact the breast, at the point surrounding the nipple, when the flange is fitted onto the woman's breast and suction is applied, at a smooth, substantially rigid, elliptical interface having no protrusions or indentations.

6. The method of claim 1 wherein placing the breast shield further comprises using a breast shield having flanges that each include a plurality of ripples on the inner wall of the flange, which ripples extend at varying radii, each of which ripples extend through an arc greater than half-way, but only partially, around the passageway, so that an area of the breast extending along an arc partially encircling the nipple contacts the ripples when the breast shield is fitted onto the breast and suction is applied.

7. The method of claim 1 wherein placing the breast shield comprises using a shield wherein the passageway surrounding the nipple, when the shield is fitted onto the breast and suction is applied, extends in a direction that is between about 20 and about 40 degrees from perpendicular to the areola.

8. The method of claim 7 wherein placing the breast shield comprises using a shield wherein the passageway surrounding the nipple, when the shield is fitted onto the breast and suction is applied, extends in a direction that is about 26 degrees from perpendicular to the areola.

9. The method of claim 1 wherein placing the breast shield comprises using a shield wherein material of the flange shaped to fit over the area centered on the areola and nipple is substantially rigid but transitions gradually to the tube, whereby abrupt edges are avoided around the nipple.

10. A breast shield comprising:
(a) a flange shaped to fit over an area centered on the areola and nipple of a woman's breast while allowing nipple and areola movement relative to the flange; and
(b) a tube extending from the flange at a portion of the flange encircling the nipple;
(c) wherein the flange and tube form a common passageway; and
(d) wherein the flange comprises a plurality of ripples on an inner wall of the flange, which ripples extend at varying radii, each of which ripples extend through an arc greater than half-way, but only partially, around the passageway, so that an area of the breast extending along an arc partially encircling the nipple contacts the ripples when the breast shield is fitted onto the breast and suction is applied.

11. The breast shield of claim 10 wherein the plurality of ripples includes three or more ripples.

12. The breast shield of claim 10 wherein the ripples extend about two thirds of the way around the passageway.

13. The apparatus of claim 10 wherein the passageway, at the point surrounding the nipple, when the flange is fitted onto the woman's breast and suction is applied, has a smooth, substantially rigid, elliptical interface having no protrusions or indentations.

14. The apparatus of claim 10 wherein material of the flange shaped to fit over the area centered on the areola and nipple is substantially rigid but transitions gradually to the tube, whereby abrupt edges are avoided around the nipple.

15. The apparatus of claim 10 wherein the passageway surrounding the nipple when the shield is fitted onto the breast and suction is applied, extends in a direction substantially non-perpendicular to the areola.

16. The breast shield of claim 15 wherein material of the flange shaped to fit over the area centered on the areola and nipple is substantially rigid but transitions gradually to the tube, whereby abrupt edges are avoided around the nipple.

17. The apparatus of claim 15 wherein the passageway, at the point surrounding the nipple, when the flange is fitted onto the woman's breast and suction is applied, has a smooth, substantially rigid, elliptical interface having no protrusions or indentations.

18. A breast shield apparatus comprising:
(a) a substantially rigid flange shaped to fit over an area centered on the areola and nipple of a woman's breast while allowing nipple and areola movement relative to the flange; and
(b) a tube extending from the flange at a portion of the flange encircling the nipple;
(c) wherein the material of the flange transitions gradually to the tube, whereby abrupt edges are avoided around the nipple;
(d) wherein the flange and the tube form a common passageway; and
(e) wherein the flange and the tube are structured to allow the passageway to contact the breast, at a point surrounding the nipple, when the flange is fitted onto the woman's breast and suction is applied, at a smooth, substantially rigid, elliptical interface having no protrusions or indentations.

19. The apparatus of claim 18 wherein the elliptical interface has a length that is about twice its width.

20. The apparatus of claim 18 wherein the flange is shaped so that an area of the breast, at least in an area below the nipple, contacts an inner wall of the flange when the breast shield is fitted onto the breast without suction being applied.

21. The apparatus of claim 20 wherein (i) the passageway surrounding the nipple when the shield is fitted onto the breast and suction is applied, extends in a direction substantially non-perpendicular to the areola; and (ii) the flange further comprises a plurality of ripples on an inner wall of the flange, which ripples extend at varying radii, each of which ripples extend through an arc greater than half-way, but only partially, around the passageway, so that an area of the breast extending along an arc partially encircling the nipple contacts the ripples when the breast shield is fitted onto the breast and suction is applied.

22. The apparatus of claim 18 wherein the passageway surrounding the nipple when the shield is fitted onto the breast and suction is applied, extends in a direction substantially non-perpendicular to the areola.

23. The apparatus of claim 22 wherein the passageway surrounding the nipple when the shield is fitted onto the breast and suction is applied, extends in a direction between about 20 and about 40 degrees from perpendicular to the areola.

24. The apparatus of claim 23 wherein the direction is about 26 degrees from perpendicular to the areola.

25. The apparatus of claim 22 wherein the flange further comprises a plurality of ripples on an inner wall of the flange, which ripples extend at varying radii, each of which ripples extend through an arc greater than half-way, but only partially, around the passageway, so that an area of the breast extending along an arc partially encircling the nipple contacts the ripples when the breast shield is fitted onto the breast and suction is applied.

26. The apparatus of claim 18 wherein the flange further comprises a plurality of ripples on an inner wall of the flange, which ripples extend at varying radii, each of which ripples extend through an arc greater than half-way, but only partially, around the passageway, so that an area of the breast extending along an arc partially encircling the nipple contacts the ripples when the breast shield is fitted onto the breast and suction is applied.

27. The apparatus of claim 18 further comprising:
    (a) a flexible strap structured to pass around the back of a woman's neck; and
    (b) a generally triangular trapeze support structure supporting the flange when the tube passes through the trapeze support structure, which trapeze support structure comprises:
        (i) a rigid bar having a first end and a second end;
        (ii) a first flexible member extending between and coupling together the strap and the first end of the bar; and
        (iii) a second flexible member extending between and coupling together the strap and the second end of the bar.

28. The apparatus of claim 27 wherein the flange further comprises a plurality of ripples on an inner wall of the flange, which ripples extend at varying radii, each of which ripples extend through an arc greater than half-way, but only partially, around the passageway, so that an area of the breast extending along an arc partially encircling the nipple contacts the ripples when the breast shield is fitted onto the breast and suction is applied.

29. The apparatus of claim 27:
    (a) wherein the strap has a first end and a second end;
    (b) wherein the trapeze support structure is coupled to the first end of the strap;
    (c) further comprising a second generally triangular trapeze support structure coupled to the second end of the strap, which second trapeze support structure comprises:
        (i) a second rigid bar having a first end and a second end;
        (ii) a third flexible member extending between and coupling together the strap and the first end of the second bar; and
        (iii) a fourth flexible member extending between and coupling together the strap and the second end of the second bar; and
    (d) further comprising a second breast shield comprising:
        (i) a second substantially rigid flange shaped to fit over an area centered on the areola and nipple of a woman's breast while allowing nipple and areola movement relative to the flange; and
        (ii) a second tube extending from the second flange at a portion of the flange encircling the nipple;
        (iii) wherein the material of the second flange transitions gradually to the second tube, whereby abrupt edges are avoided around the nipple;
        (iv) wherein the second flange and the second tube form a common, second passageway; and
        (v) wherein the second flange and the second tube are structured to allow the second passageway to contact the breast, at a point surrounding the nipple, when the second flange is fitted onto the woman's breast and suction is applied, at a smooth, substantially rigid, elliptical interface having no protrusions or indentations;
    (e) wherein the second trapeze support structure supports the second flange when the second tube passes through the second trapeze support structure.

* * * * *